United States Patent
O'Malley et al.

(10) Patent No.: US 6,541,478 B1
(45) Date of Patent: Apr. 1, 2003

(54) SMOKING CESSATION TREATMENTS USING NALTREXONE AND RELATED COMPOUNDS

(75) Inventors: Stephanie O'Malley, New Haven, CT (US); Boris Meandzija, Hamden, CT (US); Suchitra Krishnan-Sarin, Durham, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/397,570

(22) Filed: Sep. 16, 1999

Related U.S. Application Data

(60) Division of application No. 08/952,402, filed on Nov. 12, 1997, now Pat. No. 6,004,970, and a continuation of application No. PCT/US97/03831, filed on Mar. 12, 1997.
(60) Provisional application No. 60/015,706, filed on Mar. 13, 1996.

(51) Int. Cl.$^7$ .............................................. A61K 31/497
(52) U.S. Cl. .................. 514/252.15; 514/282; 514/321; 514/326; 514/398; 514/399; 514/401; 514/652; 514/657
(58) Field of Search ................................. 514/649, 282, 514/326, 252.15, 629, 401, 321, 657, 398, 399, 652

(56) References Cited

U.S. PATENT DOCUMENTS

| | | | | | |
|---|---|---|---|---|---|
| 4,217,353 A | * | 8/1980 | Smith, Jr. | .................... | 424/260 |
| 4,895,845 A | * | 1/1990 | Seed | .......................... | 514/252 |
| 4,946,848 A | | 8/1990 | Tuttle | .......................... | 514/282 |
| 5,422,356 A | | 6/1995 | Mitch | .......................... | 424/426 |
| 5,486,362 A | | 1/1996 | Kitchell | ...................... | 514/317 |

FOREIGN PATENT DOCUMENTS

WO    WO 97/18781    5/1997

OTHER PUBLICATIONS

Opitz et al, "Volitional oral intake of nicotine in tupaias: drug-induced alterations", Drug and Alcohol Dependence, 21, 1988, pp. 99–104.*
Aceto, et al., Neuropharmacol. 25:1030–1036 (1986).
Covey & Glassman, Br. J. Addiction 86:991–998 (1991).
Davenport, et al., Neurosci. Lett. 113:40–46 (1990).
Davison, et al., Clin. Pharmacol. Ther. 44:265–267 (1988).
Franks, et al., J.A.M.A. 262:3011–3013 (1989).
Glassman, et al., J.A.M.A. 259:2863–2866 (1988).
Gorelick, et al., J. Subst. Abuse 1:153–159 (1989).
Hilleman, et al., Ann. Pharmacother. 27:1025–1028 (1993).
Höllt & Horn, Clin. Investig. 70:224–231 (1992).
Houdi, et al., Peptides 12:161–166 (1990).
Hutchinson, et al., Exp. Clin. Psychopharm. 4:431–437 (1996).
Karras & Kane, Life Sci. 27:1541–1545 (1980).
Lee & D'Alonzo, Arch. Intern. Med. 153:34–48 (1993).
Malin, et al., Psychopharm. 112:339–342 (1993).
Malin, et al., Pharm. Biochem. & Behav. 53:81–85 (1996).
Nemeth–Coslett & Griffiths, Psychopharm. 89:261–264 (1986).
O'Connor, et al., J.G.I.M. 10:255–260 (1995).
Opitz & Weischer, Drug & Alc. Dep. 21:99–104 (1988).
Pauli, et al., Psychopharm. 111:472–476 (1993).
Pierzchala, et al., Peptides 8:1035–1043 (1987).
Pomerleau, et al., Add. Behav. 9:265–271 (1984).
Prochazka, et al., Arch. Intern. Med. 152:2065–2069 (1992).
Sutherland, et al., Psychopharm. 120:418–425 (1995).
Swan, et al., Add. Behav. 21:481–490 (1996).
Tripathi, et al., J. Pharm. Exp. Ther. 221:91–96 (1982).

* cited by examiner

Primary Examiner—Dwayne C. Jones
(74) Attorney, Agent, or Firm—Mary M. Krinsky

(57) ABSTRACT

Nicotine dependency is treated by administration of an opioid antagonist. In some embodiments, rapid or ultra rapid detoxification techniques include using a combination of an effective amount of an opioid antagonist such as nalmefene, naloxone or naltrexone or a mixture of any one of these, and either clonidine or related compounds either while awake, or while under sedation or anesthesia, followed by continued administration of an effective amount of an opioid antagonist with or without agents that enhance nicotine dependency treatment. Persons are also treated for nicotine dependency with more gradual detoxification methods using administration of a combination of an effective amount of an opioid antagonist such as nalmefene, naloxone, naltrexone, or a mixture of any of these, and an effective amount of agents used to treat nicotine withdrawal including nicotine, such as that delivered by a nicotine patch, nicotine chewing gum, nicotine inhaler or other methods for delivering nicotine, antidepressants and antianxiety agents, and/or clonidine and related compounds. Administration of an effective amount of an opioid antagonist to prevent relapse, attenuate craving, and reduce weight gain during and after treatment for nicotine dependency is continued in some embodiments.

19 Claims, No Drawings

SMOKING CESSATION TREATMENTS USING NALTREXONE AND RELATED COMPOUNDS

CROSS-REFERENCES TO RELATED APPLICATIONS

This application claims priority benefit of U.S. application Ser. No. 60/015,706, filed Mar. 13, 1996, and a continuation of PCT application Ser. No. PCT/US97/03831, filed Mar. 12, 1997. This application is a divisional of U.S. application Ser. No. 08/952,402, filed Nov. 12, 1997, allowed on Aug. 27, 1999 now U.S. Pat. No. 6,004,970.

This invention relates to the use of opioid antagonists such as naltrexone, naloxone or nalmephene alone or with either nicotine replacement therapy or with other withdrawal attenuating agents, to increase smoking abstinence rates, to decrease craving for cigarettes, reduce relapse to heavy smoking during detoxification or once smoking abstinence has been achieved, and to reduce weight gain associated with smoking cessation.

DESCRIPTION OF THE RELATED ART

Tobacco dependence continues to be a major health hazard for millions of Americans, and because smoking may pose a health risk for non-smokers as well, smoking cessation treatments are of great public interest.

Dependence is an adaptive biological state induced by chronic drug exposure which manifests itself in various behavioral and physiological responses when drug exposure ceases. Withdrawal from nicotine following chronic use of tobacco products results in the emergence of an abstinence syndrome which reaches its peak intensity within the first day. Cessation of smoking has been shown to result in a number of signs and symptoms of withdrawal such as increases in irritability, anxiety, restlessness, impatience, somatic complaints, cigarette craving, hunger, insomnia, tremulousness and heart rate as well as difficulty concentrating, all of which are collectively called the tobacco withdrawal syndrome.

In recent years, research efforts have focused on nicotine replacement strategies to treat nicotine withdrawal following smoking cessation. A transdermal nicotine delivery system popularly called the nicotine patch was introduced in 1992. Reported short term success rates for nicotine patch treatment range between 19% after three weeks in a study without concomitant support to 54% with support. In general, nicotine replacement results in quit rates approximately twice that of placebo patches. Detoxification using the nicotine patch may have limited success, in part, because of the long time frame (typically 8 weeks or more) specified for this procedure. Although active patch success rates at six months continue to be better than placebo, they are substantially lower than at the end of active treatment and range from 4% to 43% among active patch users compared with 0% to 30% in placebo patch users depending on the level of psychosocial treatment provided. This suggests the need for new treatments to prevent relapse following detoxification. The significant problem of weight gain observed with smoking cessation, particularly in women, has not been ameliorated by nicotine replacement strategies, and is often cited as a reason for relapse or for not attempting to quit.

The alpha-2 agonist clonidine is used in anxiety disorders and to decrease the abstinence reactions associated with opiate and alcohol withdrawal. Clonidine has also been tried as an alternative treatment for nicotine addiction. Two large placebo controlled trials of oral clonidine indicated that smoking cessation rates were no better that placebo (Davison, et al., *Clinical Pharmacol Ther* 44:265–7, 1988; Franks, et al., *JAMA* 261:3011–3, 1989). Since oral clonidine is associated with too many side effects other investigators tried to use transdermal clonidine. A double-blind randomized trial of transdermal clonidine in heavy smokers demonstrated that the success rates of smokers on clonidine was twice that in the placebo treated group (Glassman, et al., *JAMA* 259:2863–6, 1988) and a recent meta-analytic review confirms the doubling of quit rates with clonidine (Covey, et al., *Br J Addiction* 86:991–998, 1991). However, other investigators have found that transdermal clonidine attenuated nicotine withdrawal but did not increase smoking cessation (Prochazka, et al., *Arch Intern Med* 152:2065–9, 1992). A recent study of transdermal clonidine with and without behavior modification failed to demonstrate substantial benefits of clonidine over placebo. Clonidine was superior to placebo only in patients receiving behavior modification only at 6 weeks after smoking cessation (Hilleman, et al., *Annals of Pharmacotherapy* 27:1025–1028, 1993). Therefore, although clonidine is known to reduce nicotine withdrawal the efficacy of clonidine as a treatment for nicotine addiction remains controversial.

It would be desirable to have alternate treatments for nicotine cessation (detoxification) that are rapid, to prevent relapse during more gradual detoxification and after nicotine withdrawal, and to reduce weight gain typically observed during and after nicotine withdrawal.

BRIEF SUMMARY OF THE INVENTION

It is an object of the invention to provide new smoking cessation treatments.

It is a further and more specific object of the invention to provide smoking cessation treatments that yield optimal smoking cessation rates.

It is another object of the invention to provide a method for "rapid" (and "ultra rapid") detoxification from nicotine in order to shorten the time required for detoxification and to facilitate smoking cessation.

It is another object of the invention to provide a method for minimizing weight gains often associated with smoking cessation.

It is an additional abject of the invention to provide a method for preventing relapse after completion of nicotine detoxification.

These and other objects are provided by the present invention which provides methods for treatment of persons with nicotine dependency. These include methods for "rapid" (and "ultra rapid") detoxification from nicotine; methods for preventing relapse during more gradual detoxification and after cessation of nicotine intake; and methods for reducing weight gains during and after nicotine detoxification, by administration of an effective amount of an opioid antagonist such an nalmefene, naloxone, naltrexone, or a mixture of any of these. Naltrexone is used in one embodiment.

The invention further provides methods for treating a person for nicotine dependency by administering to the person a combination of an effective amount of an opioid antagonist such as naimefene, naloxone, naltrexone, or a mixture of any of these, and an effective amount of at least one other compound that enhances the nicotine dependency treatment such as an effective amount of a withdrawal attenuating agent. Embodiments include the use of nicotine, typically by employment of a transdermal nicotine delivery system, nicotine chewing gum, nicotine inhaler, other nicotine delivery methods, and/or administration of other compounds that manage nicotine withdrawal symptoms and/or enhance nicotine dependency treatment (e.g., antihypertensives, antidepressants, antianxiety agents, serotonergic agents, and the like) with an opioid antagonist; use of an opioid antagonist while the person is under sedation or anesthesia; and use of a withdrawal attenuating agent and an opioid antagonist after pretreatment with the attenuating agent.

BRIEF DESCRIPTION OF THE DRAWINGS (Not Applicable)

This invention is based upon the finding that opioid antagonists, alone or in combination with other compounds, are useful in smoking cessation treatments and prevention of relapse.

Briefly stated, in the practice of the invention, a person is treated for nicotine dependency by administering an effective amount of an opioid antagonist and an effective amount of at least one compound that enhances nicotine withdrawal such as a withdrawal attenuating agent; by administering an effective amount of an opioid antagonist while the person is under sedation or anesthesia; or by pretreating the person with an agent that attenuates withdrawal and then treating the person with an effective amount of an opioid antagonist and at least one compound that enhances the treatment. Once nicotine detoxification is complete, an effective amount of opioid antagonist is continued alone or in combination with at least one compound that enhances nicotine withdrawal in some embodiments.

As summarized above, effective amounts of opioid antagonists are employed in treatments for nicotine dependence. Any opioid antagonist may be employed; naltrexone and/or related compounds are used in some preferred embodiments, but any other class of opioid antagonists may be used instead or is addition. Naltrexone, 17-(cyclopropylmethyl)-4,5-epoxy-3,14-dihydroxymorphinan-6-one, is a congener of naloxone, 4,5-epoxy-3,14-dihydroxy-17-(2-propenyl)morphinan-6-one, having opiate-blocking activity. Naltrexone and related compounds include, but are not limited to, other structurally related opiate antagonists including naloxone, nalmefene (5α-17-(cyclopropylmethyl)-4,5-epoxy-6-methylenemorphinan-3,14-diol), and mixtures thereof. Naltrexone is used in one embodiment; nalmefene, in another; naloxone, in another.

Administration of opioid antagonists alone or in conjunction with other compounds can be local or systemic, or a combination of therapies. Systemic administration is preferred in some embodiments. Systemic administration can be via any method known in the art such as, for example, oral administration of losenges, tablets, capsules, granules, or other edible compositions; intravenous, intramuscular, or intradermal administration, e.g., by sterile injections, including depot versions; implants; parenteral administration of fluids and the like.

For local administration, an antagonist or a compound mixture are typically topically applied to the skin or mucosa in association with ;a pharmaceutically acceptable carrier in which the antagonist is dispersed or solubilized. Carriers may be aqueous compositions, lotions, creams, ointments, soaps, sustained release preparations such as nicotine patches and the like. An advantage of the invention is that where antagonists are administered in combination with nicotine or other medications used to treat nicotine and/or opiate withdrawal signs and symptoms (more fully discussed below), the antagonists can be combined with nicotine and/or other medications so that both can be administered together in a single treatment. For example, for the treatment of smoking cessation, the antagonist can be administered in a transdermal patch that also delivers nicotine, clonidine or other agents used to treat nicotine withdrawal.

Naltrexone and/or related compounds are administered to a person in amounts effective to block nicotine reinforcement during nicotine replacement therapy or other means of nicotine detoxification, to reduce weight gain associated with smoking cessation, and/or to prevent relapse after completion of nicotine detoxification. The amount of compound necessary to block nicotine reinforcement and prevent relapse during the therapeutic treatment of nicotine withdrawal, to reduce weight gain, or to prevent relapse following nicotine detoxification is not fixed per se, and necessarily is dependent upon the severity and extent of tobacco dependence, the particular compound employed, and the method of administration. In some embodiments, the compound is taken orally as a Revia® tablet. Typical doses vary from about 12.5 mg to about 150 mg, and in some cases from about 25 mg to about 50 to 100 mg. In other embodiments, smaller doses such as up to 12.5 mg, more narrowly up to 1 mg are employed.

As discussed more fully hereafter, in the practice of the invention opioid antagonists are be administered alone, or in combination with at least one withdrawal attenuating agent, which typically are other medications used to treat nicotine withdrawal signs and symptoms that enhance the efficacy of the nicotine dependency treatment, such an clonidine, acamprosate, antihypertensives, antidepressants, antianxiety agents, agents which alter serotonergic function or other agents.

For illustrative purposes, in a regimen for treatment in some embodiments using rapid detoxification, awake persons receive a protocol based on the "clonidine-naltrexone" approach developed for rapid opiate detoxification. On day 1, detoxification begins in the morning to allow for day long management of symptoms if needed. A rapid clonidine-naltrexone detoxification requires 2 to 5 days of medication treatment. On day 1 persons spend the day under observation, which can occur in outpatient or inpatient setting or in home with nursing supervision. Observation or visits on the subsequent days (days 2–5) occur for assessment of withdrawal symptoms and further administration of medications. Certain medications for control of withdrawal symptoms may be dispensed.

In some embodiments, the medication schedule for this "rapid detoxification" is as follows:

Day 1:
Clonidine or related compounds 0.1–0.2 mg initially followed by 0.1–0.2 mg every 4–8 hours for a daily total of up to 1.2 mg. Blood pressure is closely monitored and the dose regulated accordingly.

Naltrexone: 25 mg 1–4 hours after initial clonidine dose.

Day 2:
Clonidine or related compounds: 0.1–0.2 mg initially followed by 0.1–0.2 mg every 4–8 hours for a daily total of up to 1.2 mg to treat withdrawal signs and symptoms. Blood pressure is closely monitored and the dose regulated accordingly.

Naltrexone: 50 mg 1–4 hours after initial Clonidine dose.

Days 3–5:
Clonidine or related compounds: 0.1–0.2 mg at 9 a.m. followed by 0.1–0.2 mg every 4–8 hours for a daily total of up to 1.2 mg to treat residual withdrawal signs and symptoms.

Naltrexone: 50 mg at 10 a.m., one hour after initial clonidine dose.

In other embodiments, an "ultra rapid" detoxification is completed in which the person will receive "light sedation" or general anesthesia (including mechanical ventilation) followed by detoxification using full doses of naloxone, naltrexone, nalmefene, and/or a mixture of any of the above. Sedation or general anesthesia can be achieved using a variety of barbiturates, benzodiazepines, and other classes of medication commonly used for this purpose. In the case of deep sedation, respiratory depression may necessitate the use of mechanical ventilation with intubation. To minimize the risk of vomiting, premeditation with an antiemetic may be necessary. Detoxification will be achieved using naloxone, naltrexone, nalmefene or a mixture of any of these in doses similar to those described herein. For example, naloxone can be administered in doses intravenously both as a "bolus" (2 to 10 mg) and/or as a continuous drip (e.g. 0.2 to 1.0 mg/hr). Oral administration of naltrexone (e.g., 25 to 100 mg) prior to sedation/anesthesia could also be used to achieve detoxification. Naltrexone or nalmefene could also be administered intravenously.

In many of these embodiments, a more gradual detoxification from nicotine is achieved through administration of effective amounts of naltrexone and/or other compounds to a person in combination with an effective amount of nicotine for the treatment of nicotine dependency. In the practice of this method of the invention, nicotine may be administered by any conventional means, such as, for example, using a transdermal nicotine delivery system (skin patch), nicotine chewing gum, nicotine inhaler, or other nicotine delivery systems. Examples include, but are not limited to, Habitrol®, Nicoderm®, Nicorette®, Nicotrol®, and ProStep®. Typical doses vary from about 7 mg to about 42 mg, more narrowly from about 7 mg to about 21 mg.

The regimen for treatment in some embodiments involves nicotine doses that replace approximately 50% of the nicotine levels that the smoker was previously obtaining from cigarettes. For a one-pack-a-day smoker, this would be approximately 21 mg of nicotine. Heavier smokers could begin on higher doses of nicotine and/or nicotine levels could be augmented by use of nicotine gum or nicotine inhalers. The smoker is placed on the initial replacement dose for a minimum of 1 hour to 7 days prior to beginning naltrexone treatment or treatment with another opioid antagonist. Naltrexone treatment begins at either about 12.5 mg to 25 mg a day with increases up to about 50 mg within or after a week, or initially at levels of about 50 mg. Lower doses of about 12.5 or 25 mg may also be used throughout the entire treatment, or higher doses of about 100 to 150 mg. Subsequently, the dose of nicotine patch is gradually reduced every two to four weeks or as tolerated until complete nicotine abstinence has been achieved. At that time, naltrexone could be continued for anywhere from about 3 to 4 to about 12 months, the period of highest risk of relapse following complete nicotine detoxification.

In other embodiments, an opioid antagonist is administered in conjunction with an effective amount of an antidepressant or other agent known by the skilled worker to treat withdrawal, especially the depression associated with smoking cessation (such as Welbutrin®, Paxil®, Sertraline®, Buspat®, Zofran® or Prosac®). In the practice of this invention, agents to treat nicotine withdrawal such as antidepressants by any conventional means, such as, for example oral administration of tablets, capsules, granules, or other edible compositions; intravenous, intramuscular, or intradermal administration, e.g., by sterile injections, including depot versions; implants; parenteral administration of fluids and the like. These may also be administered locally.

In an alternate embodiment, gradual detoxification is completed by using combined treatment with opiate antagonists, including naltrexone, nalmefene, or naloxone, nicotine replacement strategies, such as nicotine patch, spray, lozenges, or gum, and agents which are known to the skilled workers to enhance nicotine dependency treatment such as antidepressants in order to yield optimal smoking cessation rates. This combined treatment may be initiated simultaneously. Alternatively, antidepressant therapy and/or nicotine patch therapy could be begun prior to adding opiate antagonist treatment.

In an alternate embodiment, a detoxification treatment places smokers on narcotic antagonists and instructs them to gradually reduce their cigarette consumption over time. As nicotine is less reinforcing, persons are more successful in reducing their consumption than they would be otherwise, leading to a successful abstention ultimately. Some persons may not achieve total abstinence, however, the amount smoked is reduced because nicotine is less reinforcing and thereby reductions in harm from smoking are accrued.

Although the efforts of nicotine in the central nervous system have long been recognized, the precise mechanisms involved in centrally mediated responses to nicotine are not fully understood. This is particularly true for its addictive property. While not wishing to be bound to any theory, it may be that the method of the invention functions because some of the reinforcing effects of nicotine are mediated via activation of the endogenous opioid system. This hypothesis receives support from four lines of research showing: 1) nicotine produces antinociception; 2) nicotine stimulates release of endogenous opioids; 3) apparent nicotinic-cholinergic and opioidergic interactions exist in the brain; and 4) the ability of naloxone to precipitate opiate-withdrawal like symptoms in nicotine dependent rats.

Numerous animal studies have shown that nicotine attenuates perception of pain (or produces antinociception; see, for example, Aceto, M. D., et al., *Eur. J. Phar.* 248: 333–335, 1993 and the references cited therein). A number of investigators have observed an increase in pain thresholds in smokers who smoke nicotine-containing cigarettes, compared with those who are deprived of cigarettes, or smoked non-nicotine containing cigarettes, in response to the pain of electric shocks, ice water immersion, thermal stimulation by radiant heat, and the like. Smoking has also been found to produce changes in pain threshold in deprived, minimally deprived and ex-smokers. Recently, Lane and colleagues demonstrated that it was nicotine and not any other component of cigarettes that was responsible for antinociception following smoking (Lane, J. D., et al., *Exp. Clin. Psychopharm.* 3:140–147, 1995).

In contrast, other investigators have failed to detect changes in pain perception associated with smoking or nicotine administration (see, for example, Waller, D., et al., *Psychopharm.* (*Berlin*) 79: 193–198, 1983). This inconsistency could be due to differences in the design of the studies such as how long the subjects had been deprived of cigarettes, or differences in the methods used to test pain perception.

It has been suggested that the antinociceptive effects of nicotine are mediated via release of endogenous opioids (Pauli, P., et al.; *Psychopharm.* 111: 472–476 (1993); Pomerleau, O. F., *Addict Behav.* 9: 265–271, 1991). In support of this hypothesis, nicotine antagonizes morphine-induced antinociception, and the opioid antagonist naloxone attenuates nicotine-induced antinociception in mice (Aceto, M. D., et al., *Neuropharm.* 25: 1031–1036, 1991; Tripathi, H. L., *J Pharmacol. Exp. Ther.* 221: 91–96, 1982). Davenport and colleagues have shown that pretreatment with nicotine attenuates the ability of the u-receptor antagonist B-funaltrexamine (B-FNA) to inhibit morphine-induced antinociception, suggesting that nicotine releases endogenous opioids that bind to the opioid receptors and prevent further inactivation of these receptors by B-FNA (Davenport, K. B., et al., *Neurosci. Lett.* 113: 40–46, 1990).

Acute administration of nicotine has been shown to release endogenous opioids in vitro and in vivo, in rats and humans. Hollt and Horn have demonstrated that chronic, pulsatile treatment with nicotine (similar to that achieved with cigarette smoking) results in a significant increase in mRNA for pro-opioimelanocorticotropin (POMC) in the anterior lobe of the pituitary while tonic infusion of nicotine had less effect on opioid peptide expression (Hollt, V., and Horn, G., *Clin. Inves.* 70: 224–231, 1992). POMC which is a precursor for opioid peptides such as $\alpha$-MSh and B-endorphin is topically controlled by a hypothalamic corticotropin releasing factor (CRF). Nicotine has also been shown to increase release of CRF from invitro preparations of rat hypothalamic neurons, suggesting that nicotine may be exerting its stimulatory effect at the hypothalamic level (Calogero, A. E., *Neuroendo.* 47: 303–308, 1988).

The distribution of nicotinic receptors overlaps with the localization of opioid peptides in a number of brain regions. Nicotine has been shown to release opioid peptides in many regions containing both nicotinic and opioid receptors (Pierzchala, K., et al., *Peptide* 8: 1035–1043, 1987). Nicotine has been found to increase met-enkephalin content of the opioid, met-enkephalin, in the nucleus accumbens (Houdi, A. A., et al., *Peptide* 12: 161–166, 1991), which contains enkephalin cell bodies/nerve terminals and nicotinic receptors.

Naloxone administered to nicotine dependent rats has been shown to result in behavioral signs of withdrawal which closely resemble the signs and symptoms seen during abstinence in opiate dependent rats (Malin D. H. et al, *Psychopharmacology* 112: 339–342, 1993). More recently, the ability of nicotine to attenuate the spontaneous nicotine abstinence syndrome in nicotine dependent rats has been found to be naloxone reversible, suggesting that nicotine relieves nicotine abstinence syndrome via releasing endogenous opioids (Malin D. H. et al, *Pharmacology, Biochemistry and Behavior* 53(1): 81–85, 1996).

While the aforementioned lines of evidence support a nicotine-opioid interaction, the studies on the effects of opioid antagonists on smoking behavior are inconclusive. Some investigators have found that opioid antagonists decrease nicotine self-administration in rats (Opitz, K., and Weishcher, M. L., *Drug Alcohol Dependence* 21: 99–104, 1988), and humans given short term (i.e., two hours or less) treatments of naloxone (Gorelick, D. A., et al., *J. Subst Abuse* 1: 153–159, 1989); Karras, A., and Kane, *Life Sciences* 27: 1541–1545, 1980). In contrast, other investigators have reported that opioid antagonists did not affect smoking behavior (Nemeth-Coslett, R., and Griffiths, R. R., Psychopharmacology 89: 261–264, 1986); Sutherland, G., et al., *Psyrhopharmacology* 120: 418–425, 1995). Data reported herein imply that in some cases negative effects employing opioid antagonists as a treatment that helps sustain nicotine abstinence occur because opioid antagonists appear to increase nicotine withdrawal in some persons, particularly those who abruptly quit smoking.

Results described in the Examples below show that naltrexone accelerates withdrawal from nicotine and that a combination of nicotine patch and naltrexone is superior as a smoking cessation treatment to a nicotine patch alone. Thus, effective amounts of opioid antagonists are useful in treatments far nicotine.

It is an advantage of the invention that nicotine dependent persons are rapidly detoxified from nicotine. These "rapid" and "ultra rapid" techniques result in detoxification within 1–5 days as opposed to the 6–12 weeks required of detoxification with standard nicotine replacement therapies. Thus, the "high risk" time period during which withdrawal symptoms may lead to relapse is considerably shortened. Similar rapid clonidine-naltrexone detoxification procedures have been successfully used to detoxify opiate addicts with success rates as high as 94% when compared with the 42% success rate in procedures using clonidine alone (O'Connor P G, et al., *J. Gen. Intern. Med.* 10 (5): 255–60). In some embodiments of this invention, combination therapy achieves success rates of at least about 30%, preferably at least about 90%.

It is an additional advantage of the invention that smoking abstinence is enhanced by blocking or reducing reinforcement from smoked nicotine either while on nicotine replacement therapy or other methods of detoxification or following complete detoxification from nicotine by administering effective amounts of naltrexone or other opioid antagonist. The method of the invention helps prevent relapse and reduces weight gains observed on smoking cessation by at least about 25%, preferably by at least about 50% in preferred embodiments.

The invention has very important implications for successful smoking cessation treatments. Currently the majority of smokers are unsuccessful in maintaining abstinence following a quit attempt even with the help of the nicotine patch, and weight gain is often cited as a reason for relapse or for not attempting smoking cessation. Many individuals succumb to the reinforcement derived from a single cigarette that subsequently leads to relapse. Individuals who smoke on the first day of starting nicotine patch have been found to have 10 times greater risk of relapsing to smoking (West man, et al., *Archives of Internal Medicine* 157:335–340, 1997). Naltrexone, by blocking this reinforcement, may prevent continued smoking. Since nicotine replacement therapy is generally a short-term treatment, this invention provides a method that can also be used to prevent relapse once complete withdrawal from nicotine has occurred. Use of opioid antagonists, such as naltrexone and nalmefene and other opioid antagonists, can be used in maintaining abstinence and to attenuate weight gain upon smoking cessation. Opioid antagonists can be used to support continued abstinence following detoxification from nicotine or during the detoxification process. Heretofore, there are no pharmacological interventions available for helping the person remain abstinent once detoxification is complete.

In addition, the invention is useful for developing appropriate strategies for using opioid antagonists in the treatment of nicotine dependence. Negative studies an the efficacy of opioid antagonists as treatments that help sustain nicotine abstinence are likely because opioid antagonists could increase nicotine withdrawal in individuals who abruptly stop smoking. Increased withdrawal may lead the individual to resume smoking. As a result, opioid antagonist treatment can be paired with optimal detoxification and withdrawal management strategies (i.e., optimal level of nicotine replacement, optimal duration of decreasing doses of nicotine replacement therapy, and so forth) to maximize overall quit rates by blocking reinforcement from smoked nicotine and simultaneously managing withdrawal symptomatology.

Opioid antagonists can be given simultaneously with the nicotine patch or other method of nicotine administration to gradually withdraw the person from nicotine and to prevent relapse should the person have a "slip" since opioid antagonists should also block some of the reinforcement from nicotine. To this end, opioid antagonists, for example, are given orally or combined with nicotine replacement in a transdermal delivery system. Once a person has been detoxified, opioid antagonists can be used to help maintain abstinence and prevent relapse. As mentioned above, at this time there are no agents in use to prevent relapse among individuals who have completed detoxification from nicotine using nicotine replacement strategies such as the nicotine transdermal patch, nicotine gum, or nicotine inhaler.

Opioid antagonists can also be given in combination with clonidine or while the person is maintained under sedation or general anesthesia to hasten detoxification from nicotine as has been developed for detoxification from opiates. Many individuals never complete detoxification using nicotine replacement strategies which typically take 6–12 weeks. Using the combination of the opioid antagonists and agents to treat withdrawal such as clonidine, detoxification can be completed within 3–5 days. Detoxification can be further accelerated and completed in one day using naltrexone or other opiate antagonists to precipitate withdrawal while maintaining persons under general anesthesia (as has been shown with opiate addicts).

Thus, this invention provides a variety of strategies for treating persons for nicotine dependency using alternatives to traditional management such as transdermal nicotine delivery which, as has been discussed, has met with limited success. Use of "rapid" and "ultra-rapid" detoxification techniques described above have the advantage of shortening the time course of acute withdrawal by precipitating withdrawal through the administration of opioid antagonists like those previously employed for morphine and heroin users. (See, for example, Cook, C. C., and Lipsedge, M. S., *Br. J. Hosp. Med* 38:79–80, 1987 and Presslich, O., et al., *J. Toxicol. Clin. Toxicol.* 27:263–270, 1989.) Interest in and experience with these newer detoxification techniques has increased with recent increases in drug use and the growth of managed care in the United States.

EXAMPLES

The following examples are presented to further illustrate and explain the present invention and should not be taken as limiting in any regard.

Example 1

This example describes a comparison between smoking cessation treatment with a nicotine patch alone and treatment with both a nicotine patch and naltrexone. Both groups of persons were smokers who smoked between 1 and 1½ packs per day.

Forty-nine subjects were divided into two groups. Both groups received an adequate patch dose (21 mg), and one group received, in addition, 50 mg naltrexone administered orally. Smoking cessation was determined by measurement of exhaled CO levels and number of cigarettes smoked per week. Subjects who ware only on the patch smoked on average 28 cigarettes in the second week, whereas subjects on naltrexone and the patch smoked 7 cigarettes on average. At the end of the second week, the patch group exhibited an average CO level of 4.2, whereas the naltrexone and patch group exhibited a CO level of only 1.8. The fact that the CO levels were lower in the naltrexone plus patch group suggests that subjects took in less nicotine, indicating that cigarettes may be less reinforcing for subjects on both patch and nicotine replacement. The patch only group gained an average of 2.7 pounds in two weeks, whereas the patch and naltrexone group gained an average of only 1.23 lbs. Craving for cigarettes was reduced by 30% in the naltrexone and patch group compared to the patch only group.

Example 2

This example describes a comparison between smoking cessation treatment with naltrexone alone and treatment with placebo naltrexone. Both groups of persons were smokers.

Twenty-three subjects were divided into two groups. One group received 50 mg naltrexone administered orally; the other group received a placebo. Smoking cessation was determined by measurement of exhaled CO levels and abstinence from cigarettes each week. At the end of week 1 and week 2 none of the subjects who received naltrexone were abstinent from cigarettes, whereas 1 placebo-only subject was abstinent at week 1, and 2 placebo-only subjects were abstinent at week 2. These data suggest that naltrexone when administered alone without another agent to attenuate nicotine withdrawal does not improve abstinence rates over those achieved with placebo. However, this does not preclude the use of naltrexone to decrease craving far nicotine and prevent relapse and weight gain once nicotine detoxification has been completed.

Example 3

This example illustrates that transdermal nicotine treatment attenuates withdrawal in subjects who are co-dependent on both alcohol and nicotine.

Two alcoholic smokers who experienced withdrawal when given 50 mg of naltrexone following an overnight period of abstinence from nicotine were invited back to test whether maintenance on the transdermal nicotine patch prior to taking naltrexone attenuated the side effects of naltrexone that they had previously experienced when they abstained from nicotine. Subjects received 28 mg nicotine patches for three days and on the third day they took a single dose of 50 mg naltrexone. They were observed for the next six hours. One subject who smoked 1½ packs of cigarettes per day reported no symptoms. The other subject, who smoked 2½packs per day, reported that the duration of the side effections of naltrexone was markedly attenuated. This subject also reported that he did not smoke later that day. These data suggest that nicotine patch can be combined with naltrexone to minimize opiate-like withdrawal symptoms. The first subject, who was a lighter smoker, experienced no side effects. The experience of the second subject who was a very heavy smoker suggests that either a higher dose of the nicotine patch or a lower dose of naltrexone may be needed with heavier smokers.

Example 4

An alcohol dependent who was also a smoker was prescribed naltrexone for alcoholism. The subject experienced significant nausea from the first dose of medication when he took it prior to smoking his first cigarette of the day. The severity of his nausea was such that he discontinued the naltrexone. The person was then placed on the nicotine patch in combination with naltrexone to determine whether this combined treatment attenuated the side effects observed with naltrexone, and whether this approach could help the person be abstinent from cigarettes and alcohol.

The person was prescribed 21 mg transdermal nicotine patch for four weeks. After three days on the patch, naltrexone was prescribed in escalating doses of 12.5 mg for about three days, 25 mg for about three days, followed by 50 mg daily thereafter. After about four weeks on the 21 mg patch, the patch dose was reduced to 14 mg daily for two weeks. In contrast to the person's previous experience, naltrexone was well tolerated during this six week period with only intermittent mild nausea. The person also abstained from nicotine throughout this period and did not gain any weight. These observations support the concept that the combined use of naltrexone and the nicotine patch can be done effectively with nicotine replacement and with minimal to no weight gain. When the dose of nicotine was reduced after two weeks of 14 mg nicotine to 7 mg daily, nausea reoccurred. Thus, a more gradual reduction of nicotine dose was indicated.

Example 5

In this example, naloxone challenge precipitated opiate withdrawal-like symptoms in smokers.

Four subjects between 24 and 32 years of age participated in a naloxone-challenge procedure similar to that used in studies of opioid withdrawal. Two of the subjects were smokers, smoking approximately 30 cigarettes/day and two were nonsmokers. The smokers did not differ significantly in cigarette intake or on nicotine dependence (as measured using the Fagerstrom scale).

Each subject participated in three laboratory sessions separated by at least 48 hours. On the evening prior to each laboratory session, subjects arrived at the hospital by 10 p.m. Subjects were asked to abstain from drinking alcohol, smoking and eating from the time of admission to the end of the laboratory session. The session ran from 8 a.m.–10:30 a.m. on the following morning.

Prior to the start of the lab session, abstention from smoking was verified by self-report and expired carbon monoxide (CO) levels. The two smokers had CO levels of 006 and 005 ppm and the 2 nonsmokers had CO levels of 000 ppm. All subjects were evaluated with urine drug test to confirm that they had not used opiates, marijuana or cocaine recently.

One hour prior to the start of the lab session, an intravenous catheter was inserted in the subject's non-dominant forearm vein for blood sampling and the IV was maintained with a slow drip of saline solution. Electrodes were placed on the subject's fingers to measure skin temperature and standard equipment was used to measure heart rate and blood pressure. Measures of pulse, blood pressure and skin temperature were obtained every 10 minutes prior to drug administration, every five minutes for the first half-hour following drug administration, and every 10 minutes in the second half-hour following drug administration.

Baseline measures of the Clinical Institute Narcotic Assessment (CINA) scale were obtained over a 5 minute period of 30 minutes and 10 minutes prior to naloxone administration. The study medication (saline, 0.8 mg/70 kg or 1.6 mg/70 kg naloxone) was administered intravenously at 9 a.m. Following this the severity of opiate withdrawal was assessed using the CINA, every 5 minutes for the first half-hour and every ten minutes for the second half-hour.

Both the smokers experienced a pronounced increase in withdrawal symptoms such as nervousness, restlessness, muscle tension, feeling not/cold, gooseflesh, sweating and nasal congestion in response to the highest doses of naloxone used (1.6 mg/70 kg). The lower doses of naloxone produced mild withdrawal symptoms. The total CINA scores following challenge with the highest dose of naloxone were also increased when compared with baseline. The withdrawal symptoms peaked within the first 15 minutes following naloxone challenge and had subsided within 60 minutes. On the other hand, the two nonsmokers did not display any significant increases in total CINA scores following naloxone challenge. Similar increases in single symptoms of "sweating" and "nervous", two classic signs and symptoms of opioid withdrawal were increased among the smokers but not in the nonsmokers.

The studies indicate that subjects who are dependent on nicotine evidence an opiate withdrawal-like syndrome, when challenged with an opioid antagonist. While not wishing to be bound to any theory, these data provide support for the hypothesis that nicotine dependence involves an opioid component.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

The papers cited above are expressly incorporated herein in their entireties by reference.

What is claimed is:

1. A method for treating a person for nicotine dependency and minimizing weight gain during smoking cessation therapy, comprising administering to the person undergoing such therapy an effective amount of naltrexone and another compound selected from the group consisting of clonidine, nicotine, acamprosate, bupropion, paroxetine hydrochloride, sertraline hydrochloride, buspirone, ondasetron, fluoxetine hydrochloride, and a mixture of any of these.

2. A method according to claim 1 wherein the second compound is clonidine.

3. A method according to claim 1 wherein the second compound is acamprosate.

4. A method according to claim 1 wherein the second compound is bupropion.

5. A method according to claim 1 wherein the compounds are administered in a sustained release preparation.

6. A method according to claim 1 wherein at least one third compound that enhances the nicotine dependency treatment selected from the group consisting of antidepressants, antihypertensives, antianxiety agents, agents that alter serotonin function; and mixtures thereof, is also administered to the person.

7. A method according to claim 6 wherein the third compound administered to the person is an antidepressant or an agent that alters serotonin function.

8. A method according to claim 6 wherein the third compound is administered to the person at any time before, after, or during therapy.

9. A method according to claim 1 wherein the compounds are administered simultaneously.

10. A method according to claim 1 wherein the compounds are administered sequentially.

11. A method according to claim 1 wherein the compounds are administered to the person using a method selected from the group consisting of oral administration, intravenous injection, intramuscular injection, intradermal injection, a depot version of intradermal administration, implants, parenteral administration, and combinations of these.

12. A method according to claim 1 wherein weight gains observed on smoking cessation are decreased by at least about 25%.

13. A method according to claim 1 wherein weight gains observed on smoking cessation are decreased by at least about 50%.

14. A method for treating a person for nicotine dependency and minimizing weight gain by at least about 25% during smoking cessation therapy, comprising administering to the person undergoing such therapy a combination of an effective amount of naltrexone, and an effective amount of another compound selected from the group consisting of clonidine, acamprosate, bupropion, and a mixture of any of these.

15. A method according to claim 14 wherein the other compound is bupropion.

16. A method according to claim 14 wherein the other compound is acamprosate.

17. A method according to claim 14 wherein the other compound is clonidine.

18. A method according to claim 14 wherein naltrexone and the other compound is administered in via a sustained release preparation.

19. A method for treating a person for nicotine dependency and minimizing weight gain during smoking cessation therapy, comprising administering to the person undergoing such therapy a combination of an effective amount of naltrexone and an effective of bupropion.

* * * * *

UNITED STATES PATENT AND TRADEMARK OFFICE
CERTIFICATE OF CORRECTION

PATENT NO. : 6,541,478 B1
DATED : April 1, 2003
INVENTOR(S) : Stephanie O'Malley et al.

It is certified that error appears in the above-identified patent and that said Letters Patent is hereby corrected as shown below:

<u>Column 1,</u>
Line 21, please insert the following:
-- STATEMENT REGARDING FEDERALLY SPONSORED RESEARCH The invention was made with partial government support under NIH Grant AA03510. The government has certain rights in the invention. --

Signed and Sealed this

Twenty-first Day of December, 2004

JON W. DUDAS
*Director of the United States Patent and Trademark Office*